United States Patent [19]
Mitchell et al.

[11] Patent Number: 5,422,346
[45] Date of Patent: Jun. 6, 1995

[54] INSTANT DRIED DAHLIA INULIN JUICE AND ITS METHOD OF PRODUCTION AND USAGE

[75] Inventors: Cheryl R. Mitchell; Pat R. Mitchell, both of Stockton, Calif.

[73] Assignee: California Natural Products, Lathrop, Calif.

[21] Appl. No.: 63,077

[22] Filed: May 14, 1993

Related U.S. Application Data

[63] Continuation-in-part of Ser. No. 142,561, Jan. 6, 1988, abandoned.

[51] Int. Cl.$^6$ .................. A61K 31/715; A23B 4/04; A01N 65/00
[52] U.S. Cl. .................. 514/54; 424/195.1; 424/464; 424/489; 424/78.08
[58] Field of Search .......... 424/195.1, 78.08; 514/54

[56] References Cited

U.S. PATENT DOCUMENTS

| | | | |
|---|---|---|---|
| 4,285,735 | 8/1981 | Mitchell et al. | 127/29 |
| 4,421,852 | 12/1983 | Hoehn et al. | 435/99 |
| 4,758,515 | 7/1988 | Barwald | 435/99 |
| 5,051,408 | 9/1991 | Cooper | 514/54 |

Primary Examiner—D. Gabrielle Phelan
Assistant Examiner—Peter F. Kulkosky
Attorney, Agent, or Firm—John A. Bucher

[57] ABSTRACT

A process for producing a pressed juice containing an inulin polymer mixture in a stable polymorphic form having cold water solubility according to the present invention includes the steps of pressing juice from inulin containing plants, preferably of the Compositae family and more preferably from dahlia tubers, assaying the juice to determine its initial range and distribution and processing the pressed juice under selected conditions to convert the inulin polymers of the assayed juice to an inulin polymer mixture having greater than 50% of the polymers in the range of about DP 10 to DP 45, more preferably about DP 16 to DP 40, the process including hydrolyzing inulin polymers of greater than about DP 45 into the range of about DP 10 to DP 45 to enhance permeability and unique metabolic value of the mixture as well as selectively promoting Bifidus growth in the gut. An inulin juice polymer mixture formed according to the above process is administered to individuals in selected amounts for various advantageous metabolic purposes.

43 Claims, 4 Drawing Sheets

| Average Decrease in pH of TG Medium After Incubation | | | | | | |
|---|---|---|---|---|---|---|
| (37%C for four days in anaerobic atmosphere) | | | | | | |
| | Glucose | Pure Inulin | Dahlia Juice Powder | Roasted Dahlia Juice Powder | Jerusalem Artichoke Powder | FOS |
| Average Molecular Weight | 180 | 4900 | 3980 | 1090 | 1230 | 458 |
| Typical DP Range | 1 | 9-65 | 1-55 | 1-20 | 1-20 | 2-4 |
| DP Distribution | % | % | % | % | % | % |
| 1 - 4 | 100 | 0 | 4 | 37 | 34 | 100 |
| 5 - 9 | | 0 | 8 | 39 | 36 | |
| 10 - 19 | | 11 | 26 | 23 | 27 | |
| 20 - 29 | | 34 | 29 | 1 | 3 | |
| 30 - 39 | | 31 | 19 | | | |
| 40 - 49 | | 14 | 9 | | | |
| 50 + | | 10 | 5 | | | |
| Bacterium | | | | | | |
| B. bifidum 795 | 2.25 | 0.00 | 0.50 | 1.63 | 1.13 | 1.25 |
| B. bifidum 2203 | 2.88 | 0.13 | 0.50 | 2.13 | 1.63 | 1.50 |
| B. infantis | 1.63 | 1.13 | 1.38 | 0.63 | 1.38 | 1.50 |
| B. breve | 1.38 | 0.00 | 0.13 | 1.00 | 1.13 | 1.50 |
| B. adolescentis | 0.75 | 1.25 | 1.13 | 1.00 | 1.38 | 1.13 |
| B. longum | 1.63 | 0.00 | 0.13 | 0.75 | 1.25 | 1.50 |
| B. angulatum | 1.38 | 0.25 | 0.50 | 0.25 | 1.13 | 1.13 |
| B. catenulatum | 1.00 | 0.25 | 0.63 | 0.38 | 0.63 | 1.13 |
| B pseudo-catenulatum | 1.38 | 0.13 | 0.50 | 0.13 | 1.13 | 1.00 |
| E. coli | 2.38 | 0.13 | 0.00 | 1.75 | 0.63 | 0.75 |
| Staphylococcus aureus | 2.13 | 0.50 | 0.25 | 1.50 | 1.38 | 1.88 |
| Enterobacter aerogenes | 2.13 | 0.13 | 0.88 | 1.75 | 1.25 | 1.75 |
| Enterobacter cloacae | 1.75 | 0.13 | 0.00 | 0.75 | 0.38 | 0.38 |
| Enterococcus faecium | 2.88 | 0.00 | 0.00 | 2.50 | 2.75 | 3.00 |
| Enterococcus faecalis | 3.00 | 0.00 | 0.13 | 2.25 | 1.38 | 1.63 |
| Clostridium perfringens | 2.75 | 0.13 | 0.00 | 1.13 | 1.38 | 1.75 |

| Analysis of Dried Dahlia Inulin Juice Products | |
|---|---|
| | Total per 100 grams[1] |
| Protein, gm | 4 |
| Moisture, gm | 2 |
| Ash, gm | 3 |
| Fat, gm | 1 |
| Crude Fiber, gm | 0 |
| Inulin/Inulides, gm | 80 |
| Calories (cal/100 gm)[2] | 115–385 |
| Vitamin A, IU | 535 |
| Thiamine ($B_1$), mg | 0.04 |
| Riboflavin ($B_2$), mg | 0.17 |
| Vitamin C, mg | 23 |
| Niacin, mg | 4.6 |
| Calcium, mg | 265 |
| Iron, mg | 0.7 |
| Phosphorous, mg | 260 |
| Potassium, mg | 1215 |
| Sodium, mg | 100 |

1. All values are approximate and representative but are not to be construed as specifications.
2. Lower figure based on 1.2 calories/gram inulin. disagreement exists as to caloric value of inulin.

INSTANT DRIED DAHLIA INULIN JUICE AND ITS METHOD OF PRODUCTION AND USAGE

This application is a continuation-in-part of Ser. No. 07/142,561 filed Jan. 06, 1988 and now abandoned.

FIELD OF THE INVENTION

The present invention relates to a natural juice obtained from the Compositae family which is rich in inulin. More particularly, the invention relates to a process for obtaining a dried inulin containing juice, preferably from dahlia tubers, of selected characteristics and the product of that process as well as methods of beneficial usage in (a) diabetes, (b) hypercholesterolemia, (c) weight control (d) physical stamina, and (e) selectively promoting Bifidus growth in the gut.

This is a continuation-in-part of application Ser. No. 07/142,561 filed Jan. 6, 1988 by the inventors of the present invention and now abandoned.

BACKGROUND OF THE INVENTION

Scientific information forming a portion of the basis for an understanding of the present invention has been developed over a significant period of time, in excess of 100 years. The prior art developed over that period of time is accordingly discussed in detail in order to assure its proper understanding in connection with the present invention and to assure a better understanding of the novel contribution of the present invention over the substantial body of prior art described below.

Inulin was first discovered in 1804 by separating the juice extracts from the Jerusalem artichoke and crystallizing or purifying the inulin from this juice. Being analogous to starch which is a glucose polymer, inulin is chiefly a fructose polymer. While starch is the primary storage carbohydrate in almost all grains and tubers (such as potatoes), inulin is the primary storage carbohydrate in the tubers of the dahlia (*Dahlia variablis*) and other members of the Compositae family, notably the Jerusalem artichoke (*Helianthus tuberosus*), and is found in the roots of elecampane (*Inula Ilenium*), dandelion, chicory, and salsify.

Analysis by Praznick[1] of the crude inulin obtained from these sources without purification revealed chains of varying length depending upon the source (see Table 1). He also noted that the range and distribution of the polymers was dependent not only on the source, but on the time of year that the sample was obtained as well. Tubers harvested in the fall immediately after a killing frost had longer polymers than tubers harvested in the early spring.

TABLE 1

Polymer Distribution of Crude and Purified Inulin Obtained from Jerusalem Artichoke, Dahlia and Chicory

| Inulin Source | Polymer Distribution (DP Range) | | |
|---|---|---|---|
| | (2–19) | (20–40) | >40 |
| Jerusalem artichoke | 74 | 20 | 6 |
| Jerusalem artichoke purified | 2 | 24 | 76 |
| Dahlia | 31 | 21 | 40 |
| Dahlia purified | 5 | 30 | 65 |
| Chicory | 55 | 18 | 17 |
| Chicory purified | — | — | — |

Jackson[2] reported that purification of the inulin by recrystallization from water produced a uniform product (which was hot water soluble) irrespective of the source. This agrees with the much later findings of Praznick summarized in Table 1.

The general method for the commercial preparation of inulin, as described by E. McDonald[3] of the National Bureau of Standards, involved hot water extraction of plants rich in inulin followed by the addition of milk of lime prior to filtration and precipitation of the inulin. The inulin was then recrystallized to make a purified inulin product.

The physical properties of inulin according to the Merck Index (#4872) published by Merck & Co., Rahway, N.J. include an average molecular weight of about 5,000 and solubility in hot water with very slight solubility in cold water. The USP (United States Pharmacopoeia) lists the standards for inulin which include a residue on ignition (ash) of not more than 0.05% and a completeness of solution including clarity.

Purified inulin has been utilized in the past in determination of Glomerular Filtration Rates (GFR), permeability studies (as an extracellular marker), and hydrolytic studies with regard to the commercial production of fructose from inulin. To date, the usage of inulin has been limited to purified inulin and its subsequent use as a diagnostic chemical. There has been no commercial usage of purified inulin as a therapeutic or supplementary food material, presumably due to the high cost of purified inulin. A recent proposed usage of inulin is as a fat replacer. By utilizing the fact that a 20% solution of inulin sets into a hard "pudding-like" texture having the smooth feel of fat, it was suggested that this be used in baking to replace fat.

The literature has described numerous processes for the ultimate preparation of purified inulin. A notable and unique exception is the reference by Mitchell, et al.[4], who taught the preparation of a "crude" form of inulin which had economical benefits making it feasible for consideration as a human food material. "Crude" inulin as described by Mitchell has not been purified by recrystallization. Instead, the "crude" inulin of Mitchell is precipitated from the original juices and therefore contains some of the nutrients found in the juice. This "crude" inulin, like purified inulin, has been precipitated from an aqueous solution and has the similar property of being soluble only in hot water.

Mitchell teaches that inulin as it exists in the tuber is in a soluble state. By immediately pressing the comminuted tuber, the majority of the inulin can be removed from the plant resulting in a juice rich in inulin. Subsequent cooling of the pressed inulin juice results in the precipitation of the desired "crude" inulin. Mitchell warns that if pressing is not performed immediately, the inulin begins to precipitate and separation of the inulin from the plant material becomes very difficult requiring hot water to solubilize and extract the majority of the inulin.

The solubility of inulin has never been well understood. The differences in the solubility of inulin have been described by McDonald[3], C. F. Phelps[5], and R. Hill[6]. In general, Phelps found that recrystallized inulin did not obey the phase rule and increased in solubility between 60° C. and 100° C. Phelps hypothesized that a change in structure or polymorphism occurred (as opposed to a change in polydispersity). McDonald described the different forms of inulin according to how they dissolved in water. The unstable beta form, obtained by recrystallization from alcohol, was considered more soluble and dissolved in cold water while the alpha form was more insoluble and dissolved only in hot water. Most importantly, upon standing, the more soluble beta form changed to the more insoluble alpha form.

R. Hill reported solubility of inulin based on polymer size. Hill revealed that fructose polymers having a DP value of less than approximately 15 (average MW=2500) were soluble in 20° C. water while those fructose polymers of about DP 33 were insoluble.

Importantly, it should be noted here that inulin of DP 8 and higher if precipitated from an aqueous solution, results in an inulin polymer which is not cold water soluble. Hill, who used said hydrolysis on purified inulin to degrade the polymers, believed that the shorter polymers (DP of less than 15) were inherently cold water soluble. This conclusion is questioned in consideration of the fact that Hill recrystallized these shorter polymers from alcohol. McDonald taught that a cold water soluble polymer of inulin could be formed by recrystallization from alcohol. Consequently, it is believed that Hill mistakenly attributed cold water solubility as a function exclusively of polymer size instead of polymorphism. In any case, Hill went on to show that the former polymers were readily hydrolyzed in acid (PH=1, 37° C. for one hour) while the latter were not hydrolyzed under identical conditions. Hill concurred with the popular belief that, in order for inulin to be metabolized by humans, it first had to be hydrolyzed by gastric acids to fructose, the fructose subsequently being absorbed and utilized according to this hypothesis. Hill taught that the hydrolysis of purified inulin to smaller polymers of less than DP 15 formed a product best suited for human consumption.

The tubers of the Jerusalem artichoke and the dahlia have been eaten by different cultures throughout history. However, they were never found to be very popular. The Heliamhae tribe of the Compositae family which includes the Jerusalem artichoke and the dahlia have been reposed to cause dermatitis[7]. The major sensitizing agents were found to be the sesquiterpene lactones. Patch test reactions to Compositae plants in sensitized individuals are frequently severe, vesicular or bullous, and persistent. In considering a non-purified inulin as a food material, the sensitivity that some individuals have to the Compositae family would be cause for concern.

With regard to the crude pressed juices from dahlia tubers, Jerusalem artichoke and chicory, the polymer distribution of the inulin found in these sources is significant. Before recrystallization, the polymer distribution of chicory and the Jerusalem artichoke show high levels of the smaller chains and relatively low levels of the high molecular weight polymers relative to dahlia inulin. Most of the current literature with regard to inulin refers to the Jerusalem artichoke and chicory due to the established agricultural availability of these sources. References given for dahlias are solely in regard to their consideration as an ornamental plant. Earlier work had already established dahlias as the best source of inulin but, since dahlias were not grown commercially except for ornamental purposes and the market for purified inulin was limited, the Jerusalem artichoke and chicory almost exclusively filled the world's need for purified inulin.

During the time from 1976-1992, considerable work has been reported in the literature with the Jerusalem artichoke as the general subject. Uses of the Jerusalem artichoke have been summarized in a review article by N. Kosaric, et al.[8] in 1985. The primary uses included food, fodder, alcohol production and high fructose syrup production. Most of the literature pertaining to the Jerusalem artichoke, though, concerns hydrolysis (of the inulin) and fructose production.

Literature regarding chicory yields information primarily in the area of coffee additive material as well as hydrolysis of the inulin to produce fructose for use as a sweetener.

Recent literature has revealed information which suggests the beneficial effects of Bifidus bacteria in the human gut. The Japanese have reported that fructo-oligiosaccharides up to DP=4, which have been synthesized from sucrose, are well utilized by Bifidus bacteria and have been used to promote Bifidus cultures in the gut.

Comparative feeding studies involving purified inulin, whole baked Jerusalem artichokes and fructose were performed by many researchers in the period from 1870 to shortly after the discovery of insulin. Root and Baker[9] in 1925, reported that all three substances appeared to be utilized. Blood glucose levels were found to increase the greatest with fructose and the least with purified inulin. Also it was found that the maximal respiratory quotient after ingestion of Jerusalem artichokes or inulin occurred in 2-6 hours as compared with less than two hours for fructose. Another very important finding by Root and Baker was that during the experimental days when insulin was removed from the diabetic patients, the tendency towards acidosis was counteracted by all three substances.

It was then concluded that inulin, particularly that found in the Jerusalem artichoke, was a carbohydrate that could well be tolerated by diabetics. Fructose was assumed to be the key factor responsible for the prevention of ketoacidosis in diabetics, and hence later gained recognition as the "diabetic sugar". The other advantages were attributed to a slow rate of gastric hydrolysis of the inulin followed by absorption of fructose. The soluble fiber pectin, found in the Jerusalem artichoke, was also considered to contribute to the slow absorption rate of the fructose thus preventing sharp blood glucose rises. Based on these findings, many early diabetic physicians including Root and Baker proposed the usage of inulin-containing vegetables in the diet of diabetics. Unfortunately, because of the unavailability of the tubers (potatoes) requiring drying and storage so that the individual could have a year-round supply, the large amounts required (40 to 500 grams, or one to two potatoes daily), the singularity in available form, and the recent discovery of insulin, this idea was considered impractical.

Feeding studies involving a purified inulin showed that consumption resulted in the production of large amounts of intestinal gas. Because glomerular filtration studies performed by Miller, et al.[10] showed that purified inulin was neither excreted nor absorbed by the renal tubules, it was generally assumed that purified inulin was not readily metabolized.

It is not surprising that the Jerusalem artichoke, with its polymer distribution favoring small molecular weight species, was found by Root and Baker to be well utilized as a food. The inulin polymers (later found by Praznick and others to be less than DP 10) would readily be hydrolyzed to fructose in the stomach acids and utilized as such. While it was possible to explain some of the advantages noted upon feeding purified inulin and Jerusalem artichoke by hydrolysis of inulin followed by absorption of fructose, this explanation was not totally satisfactory.

A research paper by H. B. Lewis[11] reviewed the thinking at the time (1912) with regard to the value of inulin as a foodstuff. He basically summarized the work of Miura and Mendel and Nakaseko which showed that, even under the most favorable conditions, little glycogen was formed in rabbits after feeding inulin. Since the formation of glycogen occurs rapidly after the feeding of fructose, the above researchers concluded a lack of assimilation of inulin. Lewis also stated that the results of Neubauer's work also supported the idea that inulin was not hydrolyzed to fructose. In a case of fructosuria Neubauer found no increase in the fructose content of the urine after feeding 80 grams of inulin. No inulin was found in the feces either. It was observed however, that the patient suffered from intestinal gas formation after the consumption of the inulin. It was concluded that inulin was not hydrolyzed to fructose and in fact not utilized thereby producing the observed gas formation. Lewis also pointed to the work of DuCamp who explained the absence of inulin in the feces by suggesting that B. coli communis and other intestinal bacteria decompose inulin without any production of sugar.

Overall, the results of all of the research concerned with the consumption of inulin indicated a paradox. Some feeding studies found inulin to be well utilized and assumed it to be hydrolyzed and metabolized as fructose while other results indicated that inulin could not be hydrolyzed and then metabolized as fructose. A suitable explanation that would encompass the results of all these research studies was never found.

Looking at more recent developments in carbohydrate metabolism during the past decade, phosphofructokinase has been considered the key regulatory enzyme in glycolysis and hence carbohydrate metabolism. According to a recent review by Louis Hue and Ramoff Bartrons[12], one of the most important and potent stimulators of this enzyme is fructose 2,6-bisphosphate which is made in vivo by the action of the enzyme phosphofructo-2-kinase on fructose-6-phosphate. It was shown that glucagon promotes glycogenolysis and yet inhibits glycolysis by suppressing the production of fructose 2,6-bisphosphate. Insulin acts to suppress the action of glucagon but does not actually activate the production of fructose 2,6-bisphosphate and hence glycolysis. In agreement, Simon Pilkis[13] in recent years found that certain carbohydrate disorders, such as diabetes mellitus, exhibit a lower than normal concentration of fructose 2,6-bisphosphate and thus an impairment of the efficient utilization of carbohydrates via glycolysis.

It was also known that disorders of carbohydrate metabolism such as diabetes, which result in the inefficiency to utilize carbohydrates, can cause other health problems[14]. These problems include vascular micro- and macro-angiopathies which manifest themselves as nephropathy, retinopathy, coronary artery disease, cerebral vascular disease, and peripheral vascular disease.

Overall, the prior art understanding of inulin describes a stable hot water soluble polymorphic form when recyrstallized or precipitated from aqueous solutions and an unstable cold water soluble polymorphic form when the inulin is recrystallized from alcohol. The latter polymorphic form readily converts to the hot water soluble polymorphic form upon standing. Studies to determine the metabolism of inulin have been performed either with the hot water soluble polymorphic form or whole Jerusalem artichokes. It was commonly understood that the natural flora of the human digestive tract did not possess enzymes suitable for hydrolyzing the inulin in the stomach or intestines. It was further believed that acid hydrolysis could occur to some extent but only on those polymers of less than about DP 10. Consequently, Jerusalem artichokes which have a polymer distribution predominantly in the range of less than DP 10 could be well utilized while purified inulin could not (unless first subjected to hydrolysis to fructose).

SUMMARY OF THE INVENTION

The present invention relates to the discovery of the preparation and metabolic use of a juice containing the cold water soluble polymorphic form of inulin having a polymer range between DP 1 and DP 60 and having a distribution of polymers of greater than 50% between DP 10 and DP 45.

The present invention is based upon the novel discovery that the natural juice obtained from the dahlia tuber which contains a cold water soluble polymorphic form of inulin can be preserved by evaporation and drying of the juice. While it was anticipated that inulin juice which has been dried would be hot water soluble as are all inulin products that are precipitated or recrystallized from water due to presence of the long chain inulin polymers, to our surprise, we found that the fresh juice contains a major distribution of long chain inulin polymers upon being dried, and could be reconstituted in cold water. Cold water being defined as ambient or tap water between 15° C. and 30° C. Even in spite of the fact that the analysis of the polymer range and distribution indicated a range of DP 1 to DP 60 and >50% distribution between DP 10 and DP 45. This stable cold water soluble dried juice represented a concentrated form of inulin which was found to have significant economical and physical advantages over the hot water soluble polymorphic form of inulin in the preparation of food products containing inulin. Furthermore, it was found that the dried dahlia inulin juice having a polymer range of about DP 1 to DP 60, and greater than 50% distribution between DP 10 and DP 45, more preferably DP 16 to DP 40, has significant nutritional advantages over the Jerusalem artichoke. As described in greater detail below, this dried dahlia juice containing inulin in its native cold water soluble polymorphic form and having the above polymer range and distribution, is particularly valuable for specific dietary uses such as in (a) diabetes, (b) hypercholesterolemia, (c) weight control, (d) physical stamina, and (e) selectively promoting Bifidus growth in the gut.

The present invention thus discloses a stable polymorphic form of inulin which is cold water soluble as discussed in greater detail below. The invention specifically discloses a process for forming such a stable cold water soluble inulin as either a powder or syrup. Furthermore, such a powder formed according to the present invention, for example, by spray drying or drum drying, is novelly characterized by having a moisture content of no more than about 10%, preferably no greater than 8%. Typically, a powder formed by spray drying is characterized by a moisture content of about 5% while the drum dried form of the powder typically has a moisture content in the range of about 2-4%. Similarly, the present invention also discloses a process for forming the stable cold water soluble inulin as a syrup. The syrup similarly remains stable with a moisture content of no more than about 30%, preferably about 25% in order to facilitate handling and storage of the product.

In terms of the present invention, the polymer distribution portion of the inulin juice polymer mixture having greater than 50% in the range of DP 10 to DP 45 is defined as being in a form having a metabolic value suitable for mediating or alleviating conditions such as those noted above. Preferably, the invention contemplates at least about 50% of the mixture being in the range of DP 10 to DP 45 and, more preferably, at least about 80% of the mixture being in the range of DP 10 to DP 45.

We have discovered that, in comparing the oral metabolic value of inulin with fructose, the range and distribution of the polymers is of primary importance (if the polymer size is too small, the polymers may be hydrolyzed to fructose by the gastric acids in the stomach; if the polymer size is too large, the rate of intestinal permeability or metabolism by the intestinal flora is too slow). Of tantamount importance, we have formulated and effectively utilized the hypothesis that inulin has the greatest unique metabolic value when it is not hydrolyzed by the gastric acids to fructose and utilized as such. Rather, the fructose polymers (inulin-inulides) which are not hydrolyzed to fructose by the gastric acids and yet are small enough to allow for intestinal permeability can be absorbed by the intestines and serve as a precursor to fructose 2,6- bisphosphate, the potent stimulator of glycolysis. We have also found that the longer polymers that are not absorbed and make it to the gut, can be used preferentially by some Bifidus bacteria to the exclusion of the more pathogenic bacteria.

The above hypothesis is the basis for the claimed novelty of a range and more importantly a specified distribution of inulin polymers characterized by a range of DP 1 to DP 60 and a distribution of greater than 50% of the polymer between about DP 10 to DP 45, and their advantageous use in various applications as noted above.

This novel understanding of the metabolism of inulin and its relationship to range and distribution has led to the discovery of the usage of inulin of given range and distribution for various carbohydrate metabolism disorders and related vascular diseases. Applying this novel hypothesis with the discovery for the preparation of a concentrated juice containing the cold water soluble polymorphic form of inulin, we found that relatively small amounts of inulin of the specified range and distribution described above could be used effectively in dietary suppression. Also, because of the unique metabolism of inulin upon oral ingestion, we realized that there existed distinct advantages in its dietary use in promoting physical endurance. Another discovery, independent of the proposed hypothesis of inulin was the selective promotion of Bifidus in the gut to the exclusion of pathogenic bacteria.

We have discovered that the range and distribution as well as the naturally occurring phosphorous and potassium bonds are important for the unique physical characteristics (such as the cold water soluble polymorphic form and hydrolyzability) of the inulin as found in the pressed juice of inulin bearing plants such as the dahlia. Precipitation or recrystallization of inulin from water not only changes it to a hot water soluble form, but also separates the inulin from those soluble nutrients (protein, phosphorous and potassium) that characterize the inulin juice. We have also discovered that inulin as it exists in the cold water soluble polymorphic form may be processed in such a way as to enable evaporation and control the range and distribution of the inulin polymers. This is done by first evaluating the pH of the pressed juice, and then determining the range and distribution of the inulin polymers in the juice by a unique and rapid method involving high pressure ion chromatographic (HPIC) techniques. Based on the results of these analyses, pH, time and temperature of the process conditions used in the evaporation and concentration of the pressed dahlia juice may be adjusted accordingly to obtain the desired range and distribution of inulin and allow for evaporation to greater than 20% solids based on inulin.

We have also found that freshly pressed juice containing inulin may be processed in such a way as to control the range and distribution of the inulin polymers so that, when taken orally, they can be fully utilized either by direct uptake by the hepatic portal vein or selectively utilized by the Bifidus bacteria in the gut, and with minimal formation and utilization as fructose, and consequently minimal increases of blood glucose levels. We have also found that the pressed juice may be processed in such a way that essentially all the sesquiterpene lactones may be distilled off during concentration so as to yield a dahlia juice containing inulin polymers which does not produce a positive patch test on a sensitized individual.

Essentially, we have discovered the importance of and method of preparation of long chain inulin polymers in their native cold water soluble polymorphic form having a specified DP range and distribution, in carbohydrate and Bifidus metabolism. We have discovered that native inulin of a specified DP range and distribution is suitable for use in carbohydrate metabolism disorders such as diabetes as well as related vascular complications caused by hypercholesterolemia. We have also discovered that native inulin of specified DP range and distribution may be evaporated to greater than 20% solids and subsequently dried so as to produce a convenient and concentrated juice containing the cold water soluble form of inulin which would facilitate regular oral consumption. Also, that the powder of this dried concentrated native inulin of specified DP range can be compressed into tablets without the need for tableting binder aids such as starch.

It is therefore an object of the invention to provide an inulin polymer mixture having selected characteristics as noted above together with a process for forming the inulin polymer mixture and a method of employing the inulin polymer mixture.

More specifically, it is an object of the invention to provide a process for production of a cold water soluble inulin juice polymer mixture of metabolic value by pressing the juice from plants selected to have a substantial inulin content of long chain polymers of high average molecular weight, assaying the pressed juice preferably by high pressure ion chromatographic (HPIC) techniques, determining the initial range and distribution of inulin polymers in the juice and then adjusting conditions of pH, heating and holding times so that evaporation and concentration of the juice including duration of exposure to heat could convert the inulin polymer mixture in the juice to a mixture having a substantial portion of inulin polymers in the range of DP 1 to DP 60 and a distribution of greater than 50% of the polymers in the range of DP 10 to DP 45, the process conditions being further selected and adjusted for hydrolyzing inulin polymers of greater than about DP 45 to within the range of about DP 10 to DP 45, more preferably DP 16 to DP 40 in order to promote permeability as well as selective Bifidus utilization thereby enhancing the unique metabolic value of the mixture.

Even more preferably, the juice containing inulin is obtained from plants of the Compositae family and more preferably from dahlia tubers. The processing conditions are also further selected and adjusted for preferably removing sesquiterpene lactones from the inulin polymer mixture in order to avoid reactivity in sensitized individuals.

We have found that the length of time that the product is exposed to the heat of evaporation is critical in controlling the range and distribution of the inulin polymers. It is known that there exists many types of evaporators including continuous, batch-type, falling and rising film for some examples. It is also known that evaporation can take place at atmospheric pressures or under reduced pressures where the temperature of evaporation would be significantly diminished. The type of evaporator determines the length of time and the temperature that the product is exposed to during evaporation and subsequent concentration.

When we refer to the adjusting of the process conditions including the time and temperature of evaporation in order to convert the assayed juice to an inulin juice polymer mixture having a final range of DP 1 to DP 60 and a greater than 50% distribution in the range of DP 16 to DP 45, it is intended to consider the differences in types of evaporators which may be used. For example, in general we have found that if the pressed dahlia juice after analysis has substantially all its polymers within the desired DP range, then further exposure to heat during the concentration process is undesirable in that the product will convert to shorter polymers outside of the desired DP range. Consequently, it is desirable to concentrate the pressed juice under reduced pressure thereby lowering the temperature of evaporation and limiting its exposure time to this reduced temperature. However, it should be noted that evaporation to at least 25% soluble solids is necessary under these conditions to assure the removal by distillation of the sesquiterpene lactones. Another example is if the pressed juice after analysis was found to have a large number of polymers outside the DP range of 45, then it is desirable to expose the juice to the heat of boiling and hence evaporation at atmospheric conditions at from 1 to 60 minutes so as to accomplish the breakdown of the polymers above DP 45 and removal of the sesquiterpene lactones. For example, we have found that on freshly harvested tubers, having a pH equal to 5, that 5 minutes is sufficient at atmospheric conditions to convert the polymers greater than DP 45 to within the range of DP 5 to 45.

It should be further noted that during this process of evaporation and concentration of the juice, that the cold water soluble polymorph is preserved since there is no aqueous precipitation or crystallization which would result in the hot water soluble polymorph.

These conditions are discussed in greater detail below, particularly in connection with Examples I through VII.

Additional processing conditions are set forth below to permit processing of initial juice of varying range and distribution and other conditions in order to produce the same inulin polymer mixture of preferred polydispersity as described above. In addition, still further processing conditions are described below wherein the inulin juice polymer mixture is produced in a form consisting of syrups, powders and tablets, more preferably syrups having about 25 to 80 percent soluble solids, powders of from about 50 to 200 mesh and tablets containing about 100 mg to 1000 mg of the inulin juice polymer mixture. The powder form of the inulin juice polymer mixture is also particularly adapted for being formed or pressed into tablets without the addition of a binder.

It is also an object of the invention to provide an inulin juice polymer mixture, produced for example by the process described above, suitable for uses as also described above, the inulin juice polymer mixture being characterized by its polymers being in the range of DP 1 to DP 60, and having a greater than 50% distribution in the range of DP 10 to DP 45, in order to enhance metabolic value of the mixture, the inulin polymer mixture also being characterized by substantial absence of polymers above about DP 45 in order to promote permeability and selective utilization by Bifidus bacteria.

More preferably, the inulin polymer mixture is formed from inulin bearing plants of the Compositae family, more preferably from dahlia tubers, while being in the form of syrups, powders or tablets, as described above in connection with the process of the invention.

It is yet another object of the invention to provide methods of usage by forming an inulin juice polymer mixture as described above and administering the mixture to a specified group of individuals in a selected amount, preferably from about 100 mg to about 10000 mg.

Additional objects and advantages of the invention are made apparent in the following description having reference to the accompanying drawings.

BRIEF DESCRIPTION OF THE DRAWINGS

FIG. 3 is a chart summarizing the utilization of different inulin polymers by various Bifidus bacteria as well as pathogenic bacteria. The inulin juice powder of this invention prepared from dahlia selectively promoted the growth of *B. infantis* and *B. adolescentis* while inhibiting the growth of pathogenic bacteria.

FIG. 4 is a compositional analysis of a dried dahlia inulin juice product of the present invention. Note the composition of nutrients other than inulin which are characteristic of the soluble components of a pressed juice.

DESCRIPTION OF THE PREFERRED EMBODIMENTS

Figure 1:
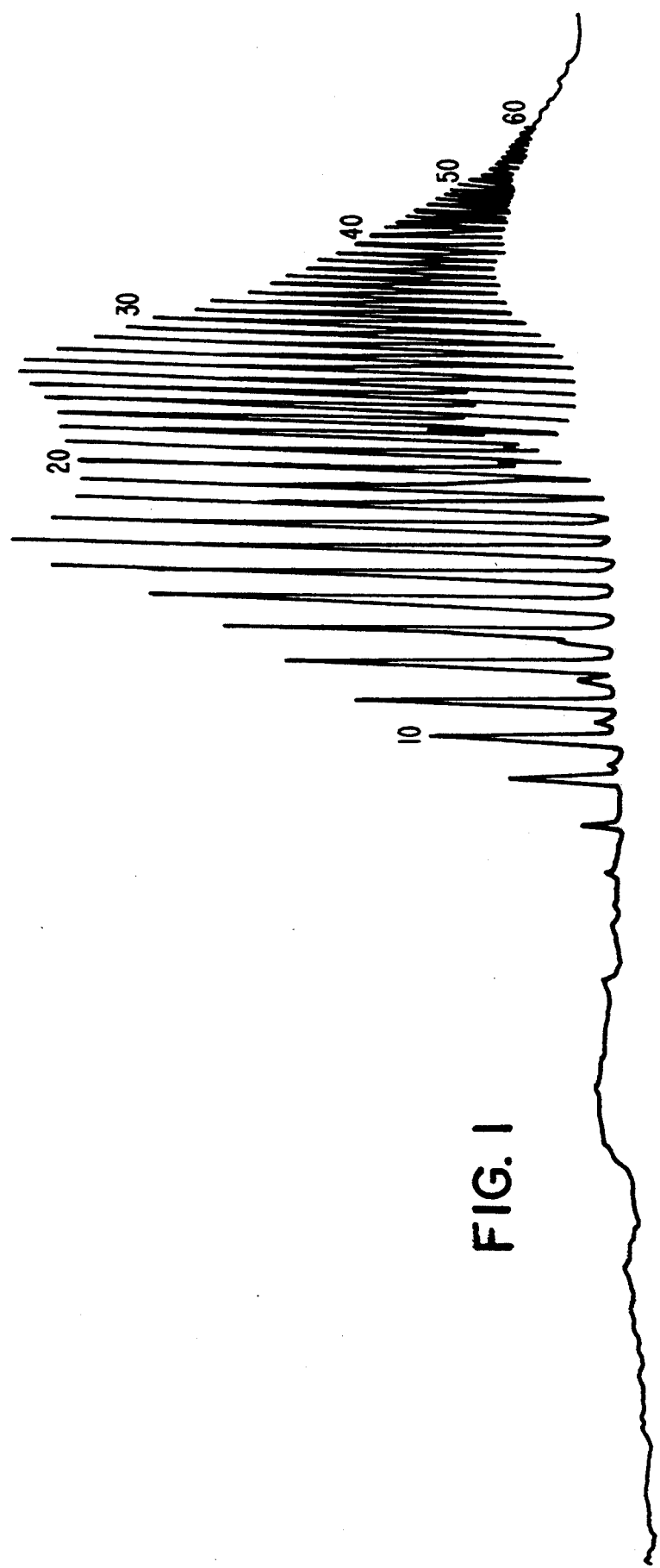
FIG. 1 is an HPIC chromatogram of commercially prepared purified inulin having less than 1 percent of the fructose polymers below DP 5, 50 percent within the range DP 5 to DP 45 and the remaining fructose polymers in excess of DP 45. Fructose polymers from DP 8 to DP 60 are characterized by individual peaks.

As noted above, the present invention relates to an inulin juice polymer mixture of selected characteristics having novel and desirable dietary uses as well as a process for forming the inulin juice polymer mixture and a method of employing the inulin juice polymer mixture.

Before proceeding with a more detailed description of the invention, it is initially noted that a number of terms are employed in connection with the present invention which may not be clearly understood or have the same meaning to those skilled in the art. Accordingly, those terms are defined below in order to assure an accurate description and better understanding of the invention.

The term "degree of polymerization" and "DP" units are employed as a measure of polymer size or chain length. The term "DP units" more particularly indicating the number of monomers in a given polymer. Thus, as an example, the range of DP 5 to DP 10 indicates a range or mixture of polymers respectively formed with from five to ten monomers. DP distribution exhibits the amount of polymers of a given size range.

The terms "inulin" and "inulide" are also used in the description of the invention together with other related terms. In a technical sense, the term "inulin" usually refers to the purified or recrystallized hot water soluble form of inulin or fructose polymers, commonly polymers of about 5400 molecular weight or larger, that is, about DP 35 and greater. At the same time, the term "inulide" is generally employed to refer to smaller polymers, for example less than about DP 35 to 40. The terms "fructosan" and "fructose polymers" are commonly employed as synonyms for "inulide".

Within the present description and for purposes of describing the present invention, the term "inulin" is intended to include all polymer links of inulin or inulides, that is, all possible DP values. Thus, the terms "inulin" and "inulin polymers" necessarily include inulides, fructosans, fructans, fructose polymers, and other similar or corresponding terms for purposes of the present invention.

This invention relates to a juice containing a fructose polymer mixture of chiefly inulin and inulides (fructose polymers), herein, "inulin", which has been processed in such a way as to retain the cold water soluble polymorphic form of the inulin, all of the natural soluble constituents such as proteins, phosphates and potassium and which has polymers within a specified range and distribution. A process for the preparation of a hot water soluble inulin polymer mixture with minor amounts of impurities has already been described by William Mitchell, et al. in U.S. Pat. No. 4,285,735 and is incorporated herein by reference. The process of our invention is described below wherein cold water soluble inulin of specified DP range and distribution is produced. A novel method of analysis for the polymer mixtures is also described.

We will also reveal the different forms such as powder, syrup and tablet that the cold water soluble inulin polymers of this invention may be consumed. We will also show that the specified inulin polymers of this invention are suitable for being compressed into tablet form without the need for a tableting aid or binder such as starch. We will also show that the inulin juice polymers of this invention can be made so that they contain essentially no sesquiterpene lactones. Finally, based on our novel understanding of the unique metabolism of the inulin polymers of this patent, the advantageous uses of inulin juice polymers in various metabolic carbohydrate disorders, related health problems such as hypercholesterolemia, physical endurance, and selectively promoting Bifidus growth in the gut.

A concentrated slurry of from 30 to 70 percent fructose polymers obtained form dahlia tubers by the method outlined by Mitchell (U.S. Pat. No. 4,285,735) has been found by the analytical method described in this invention to contain inulin polymers in the range of DP 2 to DP 60. The range and distribution of the polymers is affected by source of tubers, their age, the time of year they were harvested, storage conditions and the time between harvesting and processing. The fructose polymers obtained by the above method of Mitchell which involved precipitation of the polymers from water, were found to be hot water soluble, and while not pure, they were lacking in the quantity of the soluble protein, potassium and phosphorous found in the juice. Looking at FIG. 4, the analysis of the dried dahlia inulin juice product reveals a significant amount (in excess of 4%) of protein, ash and fat which are residual and characteristic of the dahlia juice. The amount of potassium and phosphorous are also significant. Unlike a precipitated or recrystallized inulin which would be lacking in any significant amounts of the above nutrients, the inulin juice polymers of this application necessitates the presence of these nutrients in promoting the stabilization of the cold water soluble polymorphic form and the metabolism by the Fructose 2,6 bis-phosphate mechanism proposed in this application.

What we have discovered is that polymer range and distribution can be regulated during processing without alteration of the cold water soluble polymorphic form depending on the conditions of concentration of the pressed liquors from the dahlia tuber (i.e. under vacuum or under atmospheric conditions, freshness of the pressed juice, etc.) (See Table 2 below). Under reduced pressure, concentration of the liquors does not exceed 40 percent soluble solids. At this point, solidification of the inulin/pectin material causes a non-flowable, semi-solid material similar to pudding. Reduction at atmospheric conditions readily results in soluble solids concentrations up to 70 percent, above which a semi-solid state occurs.

The inulin juice polymer mixture of this invention in syrup or powder form stabilizes the cold water soluble polymorph of inulin. The cold water soluble inulin polymer mixture in the stable form of syrups or powders is intended to mean that these forms may be stored and then later dissolved in cold water. Prior art dried inulin obtained by precipitation and recrystallization from aqueous solutions required hot water (greater than 50° C.) in order to be redissolved. If, after pressing the inulin containing juice, the juice is allowed to cool, the hot water soluble form of inulin will begin to precipitate. In the manufacture of prior art inulin (which of course is hot water soluble), the latter was always the desired process because it also separated the inulin polymers from the soluble constituents of the juice. Unlike the prior art, we found that by avoiding precipitation of inulin from the pressed juice, that the cold water soluble polymorph could be stabilized. This precipitation could be avoided by heating the pressed juice, followed by concentration and drying if desired. Hence, by this method, the cold water soluble polymorph may be stabilized in the form of syrup or powder. However, it should be realized that the conditions of concentration and drying are critical if one is to control the range and distribution mixture.

We have found it imperative to rapidly ascertain the range and distribution and preferably the pH of the pressed juice before further processing of the pressed juice. If a rapid analysis is not done on the pressed juice to ascertain the range and distribution, and the process conditions of concentration and drying adjusted accordingly, then one could not control the range and distribution of the polymers and would no doubt result in a product having the majority of polymers outside of what we believe to be the effective range of DP 10 to DP 45 and having greater than 50% of polymers between DP 10 to DP 40. It is further contemplated that these ranges and polymer distributions may be additionally defined by having an average molecular weight of between 2500 and 4500 and a median of between DP 22 and DP 35.

An example of uncontrolled concentration was given in Mitchell, et al., (U.S. Pat. No. 4,283,432) who showed that by concentrating the inulin containing juice to a 70-90 Brix syrup followed by drying, that a soluble beverage powder could be obtained. However, the range of the final product is between DP 1 and DP 20 having greater than 75% of the polymers within the range of DP 1 to DP 10.

We also found that the stable powder form of the cold water soluble polymorph was also identifiable by its moisture content. Whereas hot water soluble inulin most notably had a moisture content of approximately 12%, the spray dried cold water soluble form was found to have a moisture content of less than 10%, usually below 8% and most typically about 5%, while the drum dried form was found to have a moisture content in the range of about 2-4%.

We discovered that the pectic material in conjunction with high molecular weight species and precipitation of the hot water soluble polymorphic form is responsible for the solidification of the slurry under reduced pressures at approximately 40 percent soluble solids. Concentration at atmospheric pressures and consequently boiling temperature of 100° C. degrades the pectin and high molecular weight inulin (as well as maintaining the cold water soluble polymorphic form) so that further concentration occurs without solidification, at least up to 70 percent soluble solids. We also discovered that the pressed dahlia juice, after the soluble solids have been separated from the insoluble solids, increases in acid concentration over time. It is apparent that this acid acts to hydrolyze the inulin polymers thus producing lower molecular weight polymers. Consequently, upon concentration, higher soluble solids can be obtained before solidification occurs.

In U.S. Pat. No. 4,283,432, also by Mitchell, et al., and also incorporated by reference, it was revealed that drying of the concentrated syrup (of between 70 and 90 percent soluble solids) of Mitchell, et al. U.S. Pat. No. 4,285,735 resulted in a unique tasting beverage powder. Analysis of this beverage powder showed greater than 75% of the inulin polymers in the range of DP 1 to DP 10. We discovered that cold water soluble fructose polymers in the range of DP 5 to DP 45 can be made by co-adjusting the acid concentration in combination with the amount of heat treatment applied during the concentration of the dahlia liquors and if desired subsequent drying to produce a powder.

TABLE 2

Polymer Distribution of Some Dahlia Fructose Polymer Preparations

| Preparation | DP Ranges | | |
|---|---|---|---|
| | 0-5 | 6-45 | >45 |
| commercially prepared inulin | 0 | 35 | 65 |
| pressed dahlia juice (after 30 min) | 2 | 56 | 42 |
| pressed dahlia juice (after 12 hrs) and conc. to 80% atmospherically at 103° C.) | 70 | 30 | 0 |
| pressed dahlia juice (after 12 hrs) and concentrated to 40% under vacuum at 80° C.) | 5 | 93 | 2 |

It is important to note that, when the dahlia or Jerusalem artichoke is pressed and the resulting juice is dried to approximately 92 percent soluble solids via spray drying without prior concentration of the juice, residual amounts of sesquiterpene lactones remain so that positive patch tests in sensitized individuals result. However, when the pressed juice is first concentrated to, for example, 20 percent soluble solids thereby removing the sesquiterpene lactones by steam-distillation, negative patch tests result in sensitized individuals.

Figure 2:
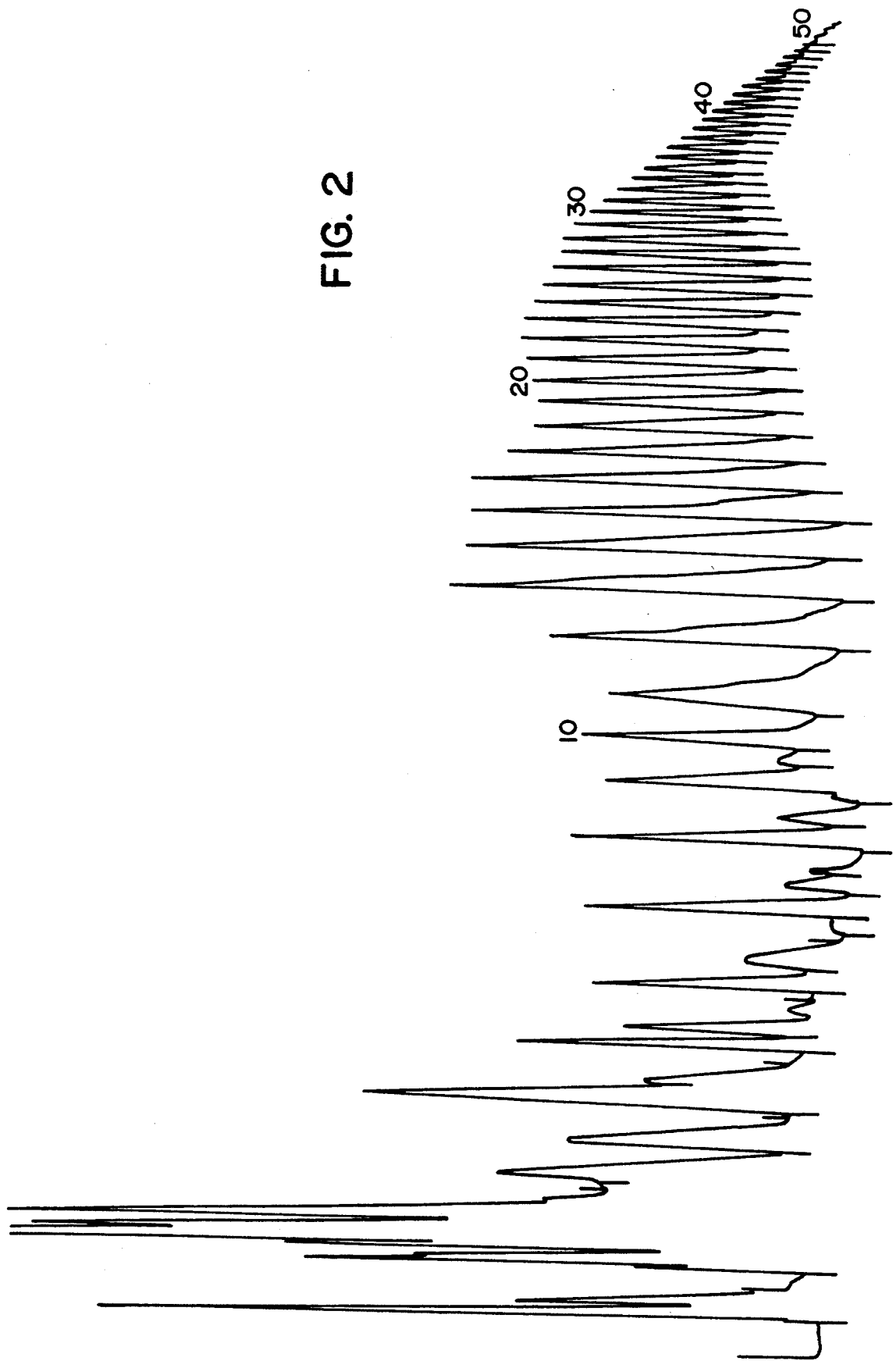
FIG. 2 is an HPIC chromatogram of freshly pressed dahlia juice. Natural constituents other than the fructose polymers are evident; however, the fructose polymers are readily discernible. Preparation of this juice and its subsequent analysis are described in Example VI. Integration results for the freshly pressed dahlia juice of FIG. 2 are recorded in Table 4.

The method of analysis used in determination of the relative distribution of fructose polymer samples is a DIONEX high pressure ion chromatograph (HPIC) with Pulsed Amperometric Detector (PAD). FIGS. 1 and 2 are reproductions of the actual chromatograms obtained using this system. FIG. 1 is a chromatogram of commercially purified inulin. As one can see, each peak is representative of a fructose polymer of a specified length or size. Taking into consideration that the PAD response is dependent upon the oxidation potential and therefore a colligative property, as the molecular weight increases with the size of each polymer, the detected response of the PAD decreases. Hence it was necessary to calculate response factors (RF) for each DP unit. These response factors were obtained by determining the response factor for fructose experimentally with a known concentration of fructose solution thus establishing it as an external standard and calculating the response factors for DP 2 through DP n by the equations below.

Assuming the molecular weight remains inversely proportional by linear relationship to the response factor, the following proportion applies:

$$\frac{RF \text{ of } DP\ n_1}{RF \text{ of } DP\ n_2} = \frac{MW \text{ of } DP\ n_2}{MW \text{ of } DP\ n_1}$$

Example:
Let $n_1$ be fructose (DP 1) with a mole wgt. of 180.
Let $n_2$ be inulobiose (DP 2) with a mole wgt. of 342.
Let RF of DP $n_1$, be 3060. This value was determined by HPIC run with a known fructose concentration by taking the observed integrated area of the fructose peak and dividing it by the known concentration to yield the RF value for fructose.

$$\frac{3060}{RF \text{ of } DP\ n_2} = \frac{342}{180}$$

RF of DP $n_2 = 1610$

The peak area of a specified DP, after integration, is divided by the response factor (as calculated above) to obtain a number which is then used in the calculation of relative weight percentage.

It was known, prior to this invention, that acid would result in the hydrolysis of purified or recrystallized inulin. It was also known that heat caused some degradation of aqueous solutions of commercially prepared inulin, liberating those polymers in the range of DP 2 to DP 8. However, it was considered desirable by those skilled in the art to avoid these conditions of hydrolysis in order to produce an optimum yield of inulin polymers having the longest possible polymer length and the narrowest possible range of polydispersity. In any case, it was not obvious to use the conditions of the naturally occurring acid of the pressed juice in conjunction with time and temperature conditions used in concentrating the pressed juices to obtain polymers within a specific DP range. We feel this conclusion was unobvious in the past due to several factors:

(1) a non-realization of the importance of inulin polymers having specified DP range and distribution; (2) the lack of a method to accurately and rapidly determine the exact range and distribution of the inulin polymers in the pressed juice; and (3) commercial usage of the purified hot water soluble polymorphic form of inulin as opposed to juice pressed from inulin containing tubers that contain cold water soluble inulin.

The Mitchell, et al. patent revealed a procedure for the preparation and concentration of the pressed juices of the dahlia tuber to yield syrups containing inulin polymers. These syrups of Mitchell have been analyzed and found to contain an inulin polymer mixture with a range of DP 1 through DP 20 with less than 25% of the polymers in the range of DP 10 to DP 20.

According to the claims of the Mitchell patent (U.S. Pat. No. 4,285,735), a 40 percent to 70 percent concentrate slurry of the fructose polymer mixture could be seeded with inulin crystals, the mixture allowed to crystallize and then subsequently dried. The precipitated or crystallized product then being the hot water soluble polymorphic form. We found this concentrate product as described by Mitchell to be unsatisfactory and undesirable because the large quantity of polymers in excess of DP 45 would result in a slow permeation rate, and residual sesquiterpene lactones from the juice made it "tainted" for human consumption. This precipitated product also did not contain the levels of protein, potassium or phosphorous found in the pressed juice.

With the aid of this new analytical technique, we were able to determine the range and distribution of polymers in the pressed juice as demonstrated in following EXAMPLES I, et al. After determining the pH of the pressed juice (hence acid concentration), and considering the range and distribution of polymers as experimentally found, adjustments of the pH and, if necessary, the time and condition of evaporation were made accordingly to produce a concentrated slurry having an inulin polymer mixture in the specified range of DP 1 through DP 60 and a greater than 50% distribution in the range of DP 10 to DP 45. For example, if a pressed juice was found to have a distribution of polymers favoring the lower molecular weight species (about 90 percent or more, less than DP 45), then concentration would be performed within 6 hours of pressing, under vacuum at between 50° C. and 85° C., for a concentration time not to exceed 1 hour.

The resulting syrup containing the inulin juice polymer mixture can be anywhere in the range of 25 percent to 80 percent soluble solids as determined by the size of the batch being concentrated and the limitation on time of concentration. This process allows for minimal exposure of the native inulin as found in the pressed juice, to such conditions as acid and heat which may further degrade it. If on the other hand, the pressed juice is found to have a distribution of polymers having a substantial quantity of high molecular weight species (about 10 percent or more, greater than DP 45), then several process options are available which would allow for the degradation of the inulin polymers by predominantly in sire acid, or by in situ acid and heat, or by predominantly heat respectively: (a) Allow the pressed juice to stand for a period of time up to 48 hours, and then concentrate under vacuum at between 50° C. and 85° C., at a concentration time of less than 1 hour; (b) Allow the pressed juice to stand for a period of time less than 6 hours, and then concentrate under vacuum and/or atmospherically at temperatures between 50° C. and 120° C., and a concentration time of less than 1 hour; or (c) Concentrate the pressed juice immediately at atmospheric conditions, at temperatures between 100° C. and 120° C. for a period of time less than 1 hour.

In those cases where there are significant amounts of polymers less than DP 5 (greater than 10 percent), it may be necessary and desirable to stabilize the pH of the juice preferably by ion exchange methods and possibly by addition of base to limit acid degradation of the smaller inulin polymers. Once the juice has been stabilized to a pH of about 7, it is possible to allow the juice to stand up to 48 hours before being concentrated under reduced and/or atmospheric conditions. The conditions of concentration being subject to those given earlier with regards to the amount of polymers in excess of DP 45 found in the juice.

The syrups which result under the process options listed in (a), (b) and (c) above are between 25 percent and 80 percent soluble solids depending on the size of the batch being concentrated and the limit on time of concentration. These polymer mixtures obtained in syrup form, ranging from 25 to 80 percent soluble solids, can be subsequently spray or dram dried by conventional methods to yield a beige powder of 50 to 200 mesh size and moisture content no greater than 10 percent. To our surprise, this powdered form of the specified inulin polymer mixture could then be tableted by compression with conventional tableting equipment without the need for additional tableting aid, to produce a 500 mg tablet the approximate size of a standard aspirin tablet. The absence of a tableting aid is advantageous when one considers the current market demand for "pure and natural" products without any unnecessary additives.

Thus, the present invention discloses a novel process for forming a stable cold water soluble polymorphic form of inulin as a powder characterized by a moisture content no greater than about 10%, more preferably about 8%. When the powder is formed by spray drying, it is typically characterized by a moisture content of about 5%. When the powder is formed by drum drying, it is typically characterized by a moisture content in the range of about 2–4%. Similarly, the present invention thus discloses a process for forming a stable cold water soluble polymorphic form of inulin as a syrup which remains stable with a water content of no more than about 30%, preferably no more than about 25% in order to facilitate storage and handling of the syrup. The powder and syrup forms of the juice containing inulin polymers produced by the processes of the present invention are similarly novel and advantageous, for example, when used in cold drink mixes and the like.

As noted above, early reports by Root and Baker suggested the eating of dried Jerusalem artichokes. However, the high percentage of dietary fiber contained in the Jerusalem artichoke tubers make them a very bulky item to consume. When considering the very low bulk density of dried and ground Jerusalem artichoke or dahlia, the amount of fructose polymers normally consumed would be minimal (less than 0.1 gram per tablespoon). Therefore, this "fibrous" form of fructose polymers would not be convenient or practical for the use of inulin as described in this invention.

The pressed juice of the Jerusalem artichoke would also not be desirable for the unique metabolic usages as described in this application because of the small quantities of polymers in the range of DP 10 to DP 45 (less than 30 percent possible) and the presence of sesquiterpene lactones. The beverage powder product of Mitchell, et al. (U.S. Pat. No. 4,283,432) would also not be desirable because of its substantial levels of inulin polymers below DP 10 (approximately 75 percent), and less than 25% inulin polymers in the DP 10 to DP 40 range.

The use of the inulin juice polymer mixture of the invention for carbohydrate disorders is based on the following discoveries:

(1) Purified inulin prepared by extraction of an inulin containing plant with hot water and alkali followed by recrystallization from water, results in an inulin which is insoluble in cold water and lacks phosphorous and potassium. Alkali or acid treatment of the extracted juice followed by crystallization results in an inulin which is morphologically different from "native" inulin and consequently has different physical properties;

(2) Inulides having a degree of polymerization (DP) of less than 10, can be readily hydrolyzed to fructose during normal digestion. However, longer chains in excess of 10 are not readily hydrolyzed by the stomach acids during average residual digestion times but are utilized based on their molecular weight and relative rate of permeability. Too long of a chain (greater than DP 45) results in a slow rate of permeability and utilization by desirable intestinal flora;

(3) A pressed juice containing a fructose polymer mixture having a distribution predominantly (greater than 50%) within the range of DP 10 to DP 45 can be absorbed by the intestines and taken up by hepatic cells or utilized preferentially by Bifidus bacterium. In the former case, it appears to be converted under physiological conditions in the presence of phosphorylase enzyme and excess inorganic phosphate to fructose 2,6-bisphosphate. Fructose 2,6-bisphosphate is known to be a potent stimulator of glycolysis; and (4) A pressed juice containing a fructose polymer mixture having a distribution predominantly (greater than 50%) in the range of DP 10 and DP 45, and preferably DP 16–40, may be used in metabolic carbohydrate disorders such as diabetes, where there has been shown to be a deficiency or ineffective level of fructose 2,6-bisphosphate. The pressed juice containing the inulin polymer mixture as described may also be used in those instances where the benefits of elevated fructose 2,6-bisphosphate levels and hence increase in glycolysis may be shown to be desirable such as in appetite depression and hence weight control, and the treatment of related carbohydrate metabolic disorders such as macro- and microangiopathies. In general, it has been recognized that the efficient utilization of carbohydrates appears to be an important factor in the lowering of serum blood cholesterol and triglyceride levels. By being a precursor to the potent stimulator of glycolysis, it is well within reason to assume that inulin then aids in the efficient utilization of carbohydrates.

(5) Well known to those skilled in the an are the health advantages of a predominant culture of Bifidus bacteria in the gut. By providing the gut with a nutrient that is well utilized by the Bifidus bacteria found in the human gut and not utilized by more pathogenic bacteria, then the growth of the Bifidus bacteria will be selectively promoted. The results in FIG. 3 demonstrate the utilization by *Bifidus infantis* and *Bifidus adolescentis* of glucose, pure inulin, dahlia inulin juice powder (made according to the process of this application), Jerusalem artichoke flour, and fructo-oligiosaccarides (FOS). The roasted dahlia juice powder of the Mitchell patent, could only be utilized by *B. adolescentis*. The experimental results in FIG. 3, gives the decrease in pH of a prepared medium after incubation with a variety of different bacteria that are naturally occurring in the gut. If the decrease in pH is less than 0.50, then the bacteria was not able to significantly utilize the carbohydrate test material and therefore the growth of the bacteria was impeded. Both the pure inulin and the inulin juice polymers of this application (prepared from dahlia tubers) were well utilized by *B. infantis* and *B. adolescentis* which are both Bifidus cultures that naturally occur in the human gut. More importantly, other bacteria in the gut which are considered pathogenic such as *Escherichia coli, Staphylococcus aureus, Enterococcus faecium, Enterococcus faecalis* and *Clostridium perfrigens* could not readily utilize either the pure inulin or the dahlia inulin juice polymers. These same bacteria could however, due to the predominance of polymers less than DP 10, readily utilize for the most part glucose, roasted dahlia juice powder of the Mitchell patent, Jerusalem artichoke powder and the small chain Fructo-oligiosaccharides (FOS). These results strongly suggest that Bifidus growth could be selectively promoted in the gut by pure inulin or the dahlia inulin juice powder of this application.

Having outlined the steps in our invention, we will now give in detail, by example, (I) the process for production of a pressed juice containing a cold water soluble fructose polymer mixture of specified DP range and distribution and containing no sesquiterpene lactones, (II) analysis of the polymer mixture specifying conditions of analysis, (III) preparation of the pressed juice containing fructose polymer mixture into convenient, cold water soluble, concentrated and measurable forms such as syrups, powders and tablets. Specific dietary utilization of these specified polymers includes:

a. diabetesmellitus;
b. weight control via appetite suppression;
c. enhancing physical endurance; and
d. selective promotion of Bifidus growth in the gut.

EXAMPLES I–III

Method of Production of a Pressed Juice Product Containing a Cold Water Soluble Fructose Polymer Mixture Having a DP Range Within DP 1 to DP 60 and Having Greater Than 50% of the Polymer in the Range of DP 10 to DP 45 and Containing no Sesquiterpene Lactones For each of Examples I–III, freshly dug, turgid, dahlia tubers (1.2 kg) were washed and scrubbed in cold water. One kg of the scrubbed tuber was ground in a Waring Blender to the consistency that would allow the slurry to pass through a number 10 U.S. Standard sieve. The ground material was filtered through three layers of cheese cloth (to remove insolubles), and finally pressed to remove the remaining solubles. The pressed juice was brought to 100° C. and the surface skimmed to remove protein coagulum. A yield of 700 ml of a clear liquid was obtained which contained 17 percent soluble solids. The range and distribution of inulin polymers of this freshly dug and pressed dahlia juice was determined by Example VI and is summarized in Table 3 below.

Based on the range and distribution of inulin polymers as found in Example VI, the following process variations were then performed:

EXAMPLE I 200 ml of the above juice were allowed to stand at room temperature for 48 hours before concentration under reduced pressure (at a temperature of 50° C.) for 1 hour to a concentration of 40 percent soluble solids. The polydispersity of this product is summarized in Table 3 below. The concentrate was then spray dried and processed to a beige powder of from 50 to 200 mesh having a moisture content of 5 percent.

EXAMPLE II 200 ml of the above juice were allowed to stand for 6 hours at room temperature before concentration at atmospheric pressure and a temperature of 100° C., for a period of 30 minutes, to 55 percent soluble solids. The polydispersity of this product is summarized in Table 3 below. The syrup was then spray dried and processed to a beige powder of from 50 to 200 mesh and 5 percent moisture.

EXAMPLE III 200 ml of the above juice were immediately concentrated at atmospheric pressure, reaching a final temperature of 120° C., for a period of 1 hour, to 80 percent soluble solids. the polydispersity of this product is summarized in Table 3 below. The syrup was then drum dried and processed to yield a beige powder of from 50 to 200 mesh and 4 percent moisture.

EXAMPLES IV-V

For each of EXAMPLES IV-V, two week old dahlia tubers which had been stored at 50° C. (1.2 kg) were washed and scrubbed in cold water. One kg of the scrubbed tuber was ground in a Waring Blender to a consistency allowing the slurry to pass through a number 10 U.S. Standard sieve. The ground material was filtered through three layers of cheese cloth (to remove insolubles), and finally pressed to remove the remaining solubles. A yield of 700 ml of clear liquid was obtained which contained 15 percent soluble solids. The polydispersity of this juice as determined by the method outlined in Example VI, is summarized in Table 3 below.

Based on range and distribution of inulin polymers, the following process variations were then performed.

EXAMPLE IV 200 ml of the latter juice were allowed to stand at room temperature for 6 hours before concentration under reduced pressure (at a temperature of 50° C.) for a period of time equal to 1 minute, to a concentration of 25 percent soluble solids. The polydispersity of this product is summarized in Table 3 below.

EXAMPLE V 200 ml of the latter juice were immediately concentrated under reduced pressure at a temperature of 85° C., for a period of time equal to 5 minutes, to a concentration of 40 percent soluble solids. The range and distribution of this product is summarized in Table 3 below.

Examples I-V illustrate one condition tending to affect the range and distribution of inulin polymers in the juice obtained from dahlia tubers. As indicated above and in Table 3 below, Examples I-III were carried out by pressing juice immediately from freshly dug dahlia tubers. By contrast, Examples IV and V were carried out by pressing juice from dahlia tubers which were stored for two weeks at about 50° C. after being dug. Table 3 illustrates the change in range and distribution of the inulin polymers for the two conditions. Generally, it may be seen from the results of Table 3 that there is an increase in polymers in the range of DP 10 to DP 45 in the dahlia tubers during storage.

Although the distribution of polymers for Examples IV and V illustrates a greater number of polymers within the preferred range of DP 10-45, Examples I-V illustrate a preference according to the present invention for pressing juice from freshly dug dahlia tubers. This preference arises since, although juice from the freshly dug dahlia tubers exhibits a lower percentage in the preferred range of DP 10-45, the substantially greater amount of inulin polymers of greater than 45 can be reduced to within the desired range of DP 10-45 according to the present invention which includes the elimination of sesquiterpene lactone.

The preceding examples also illustrate another possible variation according to the present invention wherein protein was not removed from the juice in Examples IV and V. By contrast, the procedure described for Examples I-III does include removal of protein from the pressed juice.

Examples I-VII, taken together with Table 3 also illustrate a particularly novel feature of the invention. In accordance with the preceding description, it may be seen that the pressed juice employed in each of these examples is initially assayed (preferably by HPIC techniques) to determine initial range and distribution of the inulin polymers in the juice pressed from the dahlia tubers. Processing conditions are then adjusted in order to realize maximum or optimum conversion or maintenance of inulin polymers having greater than 50% within the preferred range of DP 10-45.

Example VIII set forth below further illustrates a similar ability to assay pressed juice from dahlia tubers and select and adjust processing conditions for converting or maintaining inulin polymer within a more preferred range of DP 16-40.

The examples also illustrate a preference in the present invention for avoiding the condition of contaminating chemicals, particularly acids or bases, during processing in order to avoid removing the soluble non-carbohydrate characteristics of the juice including phosphorus or potassium content from the inulin. The maintenance of this content within the inulin is important for allowing it to achieve the desired unique metabolic usages described above.

In severe cases, it may be preferable to neutralize an existing acid pH, preferably by ion exchange. In such severe cases, it is further considered possible to employ a base for adjusting pH in the juice or inulin product as necessary. However, the addition of an alkali agent is preferably avoided under all conditions for the reasons set forth above.

TABLE 3

| | Distribution of Fructose Polymers | | | |
|---|---|---|---|---|
| Example | 1–4 | 5–9 | 6–45 | >45 |
| Freshly dug and pressed dahlia juice | 2 | 5 | 51 | 42 |
| I, II and III | <5 | 5 | >70 | <10 |
| Two week old dahlia tubers stored at 50° C. & pressed | 4 | 10 | 76 | 9 |
| IV and V | <10 | <40 | >50 | 0 |

EXAMPLES VI–VII

Analysis of the Specified Inulin Polymers of This Invention

EXAMPLE VI

A 50 ml sample of the pressed juice as initially obtained in each of Examples I–III containing 17 percent soluble solids, was pipetted into a 100 ml volumetric flask and brought to volume. A 100 μl aliquot of this 85 mg/ml solution was taken out and added to 5 ml of 0.1N NaOH. This sample solution was then passed through a C-18 PRESEP ™ filter to remove the majority of proteinaceous material and then through a 0.45 Gelman filter disk to remove any residual particulate matter. The sample was then injected into a DIONEX HPIC unit equipped with PAD detector, gold electrode, CARBOPAC I column and gradient pump. The sample was eluted with eluant A (0.1N NaOH) and eluant B (0.1N NaOH, and 0.1N NaOAc) at a gradient of 0–70 percent B in 80 minutes yielding the chromatogram in FIG. 2 and integration results in Table 4.

TABLE 4

| Polymer Description | Fresh Pressed Dahlia Juice* - Relative Weight % | Powdered Inulin Polymer Mixture** - Relative Weight % |
|---|---|---|
| Fructose | 0 | 0.3 |
| DP = 2 | 0.1 | 0.1 |
| DP = 3 | 0.1 | 0.5 |
| DP = 4 | 0.1 | 0.3 |
| DP = 5 | 0.1 | 0.3 |
| DP = 6 | — | 0.3 |
| DP = 7 | 0.2 | 0.4 |
| DP = 8 | 0.3 | 0.5 |
| DP = 9 | 0.4 | 0.6 |
| DP = 10 | 0.6 | 0.7 |
| DP = 11 | 0.7 | 0.7 |
| DP = 12 | 0.9 | 1.1 |
| DP = 13 | 0.8 | 1.1 |
| DP = 14 | 0.8 | 1.3 |
| DP = 15 | 0.9 | 1.4 |
| DP = 16 | 0.9 | 1.6 |
| DP = 17 | 0.9 | 1.7 |
| DP = 18 | 1.0 | 1.8 |
| DP = 19 | 1.0 | 1.8 |
| DP = 20 | 1.2 | 2.0 |
| DP = 21 | — | 2.0 |
| DP = 22 | 1.2 | 1.9 |
| DP = 23 | 1.2 | 1.8 |
| DP = 24 | 1.3 | 2.6 |
| DP = 25 | 1.4 | 2.9 |
| DP = 26 | 1.5 | 3.1 |
| DP = 27 | 1.6 | 3.2 |
| DP = 28 | 1.6 | 3.4 |
| DP = 29 | 1.7 | 3.4 |
| DP = 30 | 1.8 | 3.5 |
| DP = 31 | 1.9 | 3.6 |
| DP = 32 | — | 3.7 |
| DP = 33 | 2.2 | 3.8 |
| DP = 34 | 2.2 | 3.9 |
| DP = 35 | 2.3 | 3.7 |
| DP = 36 | 2.3 | 3.8 |
| DP = 37 | 2.4 | 3.8 |
| DP = 38 | 2.4 | 3.6 |
| DP = 39 | — | 3.6 |
| DP = 40 | 2.8 | 3.2 |
| DP = 41 | 2.7 | 3.1 |
| DP = 42 | 3.0 | 2.9 |
| DP = 43 | 3.0 | 2.3 |
| DP = 44 | 3.0 | 2.3 |
| DP = 45 | 3.3 | 1.8 |
| DP = 46 | 3.1 | 1.3 |
| DP = 47 | — | 0.9 |
| DP = 48 | 3.7 | 0.3 |
| DP = 49 | 3.5 | — |
| DP = 50 | 3.6 | — |
| DP = >50 | 28.3 | 0 |
| Total | 100.0 | 100.0 |

*Fresh Pressed Dahlia Juice - reference Example VI and FIG. 2 of this application
**Powdered Inulin Polymer Mixture - reference Example VII of this application.

EXAMPLE VII 7.50 grams of the dried powder of Example III were dissolved in distilled water in a 100 ml volumetric flask and brought to volume. A 100 μl aliquot of this 75.0 mg/ml solution was taken out and added to 5 ml of 0.1N NaOH. This sample solution was then passed through a C-18 PRESEP ™ filter to remove the majority of proteinaceous material and then through a 0.45 Gelman filter disk to remove any residual particulate matter. The sample was then injected into a DIONEX HPIC unit equipped with PAD detector, gold electrode, CARBOPAC I column and gradient pump. The sample was eluded with eluant A (0.1N NaOH) and eluant B (01.N NaOH, 1.0N NAOAc) at a gradient of 0–70 percent B in 80 minutes yielding the integration results listed in Table 4.

In the figures, FIG. 2 demonstrates that polymers of about DP 1 to about DP 55 can be discerned by means of HPIC.

FIG. 1 was similarly prepared as FIG. 2 and under the same conditions ad Example VII but with commercially prepared inulin instead of the dried powder of Example VII. Otherwise the conditions for FIG. 1 are as follows:

Chromatographic Analysis of Purified Inulin

SAMPLE: PURIFIED INULIN ($H_2O$ washed)
ELUANT A: 0.3% in 100 mM NaOH
ELUANT B: 100 mM NaOH
GRADIENT: 100 mM NaOH, 1.0M NaOAc
FLOW RATE: 0–70% B in 80 mins.
DETECTOR: PAD (GOLD)×3KnA
COLUMN: AS6
CHART SPEED: 0.5 mm/min.

EXAMPLE VIII

The procedure of Examples I–III was repeated whereby the juice was pressed from freshly dug, turgid dahlia tubers and assayed by HPIC methods. 200 ml of the aforementioned juice was immediately concentrated under reduced pressure at 60° C. for a period of time less than one hour up to a concentration of 40 percent soluble solids. The liquor was then further concentrated under atmospheric conditions to a final concentration of 75 percent soluble solids and a temperature of 120° C. for a period of time less than one hour. The distribution was found to have 70 percent of the fructose polymers within the range of DP 10 to DP 40. The syrup was then drum dried and processed to yield a beige powder of from 50 to 200 mesh and 12 percent moisture.

Examples IX–XVI, as set forth below, illustrate applications or methods of dietary usage taking advantage of the desirable unique metabolic and physical characteristics of the pressed juice containing the inulin polymer mixture of the present invention. The following examples also illustrate generally preferred amounts for each of the listed applications. Further, note that Examples IX–XI illustrate different methods of preparation for dietary oral convenience, preferably in the form of syrup, powder and tablets. Examples XII–XVI illustrate methods of usage and amounts for specific dietary needs. In particular, Examples XII–XVI relate to usage of the inulin polymer mixture in specific dietary applications. In these examples, the pressed juice containing the cold water soluble inulin polymer mixture makes up the entire contemplated oral amount although the mixture could of course be combined with carriers or the like if necessary.

EXAMPLES IX–XI

Preparation for Metered Oral Consumption

EXAMPLE IX

A syrup containing 80 percent soluble solids was taken by using the product of Example III by itself. A teaspoon of this syrup was equivalent to 2.5 grams of dry cold water soluble inulin polymer mixture.

EXAMPLE X

A powder containing 95 percent soluble solids obtained from Example II was taken by blending into 250 ml cold water and drinking. A teaspoon of this powder contained 4 gram of native fructose polymer mixture.

EXAMPLE XI

The powder from Example III above was taken and compressed on standard tableting equipment with no compressing aid to form a 500 mg tablet which was the size of an aspirin.

Example XI particularly illustrates the unexpected discovery that the powdered form of the inulin polymer mixture of the present invention is capable of being compressed into tablets without the need for an additional tableting aid or binder. As was also noted above, this is particularly advantageous to permit preparation of tablets including only "pure and natural" products without unnecessary additives or diluents.

EXAMPLES XII–XVI

Usages of Pressed Juices That Contain Cold Water Soluble Inulin Polymers Having Greater Than 50% of the Polymers in the Range of DP 10 to DP 45 in Specific Dietary Applications.

Based upon the hypothesis that inulin, not hydrolyzed by the gastric acids and small enough to have a significant rate of permeability, serves as a precursor to the potent stimulator of glycolysis, relatively small amounts of inulin composed of the specified polymers would be required. We experimentally found that the dosages revealed in the following examples were sufficient to affect a result.

EXAMPLE XII

Usage in Diabetes Mellitus—Root and Baker prescribed the consumption of Jerusalem artichoke tubers in the amount of 40 to 500 grams per day as a primary replacement for carbohydrates. In considering 100 g per day of Jerusalem artichoke, equivalent amount of pressed juice containing the range and distribution of inulin polymers of this invention would be 3.75 grams per day (dry weight basis).

In our experiment, five individuals who suffered from diabetes mellitus were given two, 500 mg tablets as prepared in Example XI before every meal in addition to their regular insulin injections (a total amount equivalent to 3 to 4 grams per day). Results similar to those obtained by Root and Baker for much larger doses of Jerusalem artichoke were observed. The subjects demonstrated no unusual increases in blood sugar levels upon digestion of the inulin polymer mixture of this invention; no glucose in the urine (glucose free before the test); no gas formation; an ability to consume additional glucose and sucrose items without increases in blood glucose levels or glucose in the urine. In one case, the diabetic was able to cut her insulin dosage by 50 percent without increasing her blood glucose level or glycosuria. In general, these diabetics felt that more carbohydrates could be consumed without increasing current dosages of insulin and they believed they had a greater resistance to blood glucose swings.

The above example shows how a relatively small quantity (6 to 8 aspirin-size pills) could be used to replace a substantial quantity (100 grams) of Jerusalem artichoke and have similar benefits as has already been noted for diabetics.

EXAMPLE XIII

Use of Inulin Polymers in Weight Control—The initial study group consisted of 20 overweight females who were placed on a 600–1000 calorie diet which consisted of 70–75 percent complex carbohydrates, 14% protein and 11% fat. The controls and the study population were maintained on the same protocol throughout the two month investigation. The inulin juice powder of this invention was the only variable used in the study group. Each subject in the study group was instructed to take 2–3 dahlia inulin juice tablets (500 mg each) prior to each meal and on a PRN basis to suppress hunger. At the end of the two month study period, the study group averaged a 24 pound weight loss as compared to an 18 pound average weight loss in the control group. 100 percent of the study population reported minimal to no hunger during the two month period and serum glucose levels maintained a consistent 100–105 mg/dl while the control's averaged 90 mg/dl. 80 percent of the controls complained of difficulty controlling hunger during the study period. Fasting serum glucose levels were drawn weekly.

Results of this study indicate that inulin demonstrates an effective means of suppressing appetite and controlling serum glucose levels. The inulin tablets were also used with two reactive hypoglycemics who both have demonstrated significant remission of symptomatology after following the aforementioned protocol. The reactive hypoglycemic subjects were not in the weight management group.

In an attempt to eliminate bias and placebo effect, the patients were not told the reason for taking the inulin tablets except for the fact that it was a supplement to be used with their weight control protocol.

EXAMPLE XIV

Usage in Vascular Disorders—The inefficient utilization of carbohydrates is one of the causes for the buildup of cholesterol in the arteries resulting in heart disease and other vascular complications. Accordingly, the pressed juice containing the inulin polymer mixture of this invention having greater than 50% inulin polymers in the range of DP 10 to DP 45 is believed to stimulate glycolysis and therefore the utilization of carbohydrates. The effect of this improved utilization in some individuals is to lower blood cholesterol values.

Using a double blind parallel design, 12 subjects were randomized, based on screening cholesterol values, sex, and age, into two groups for the four week study. There were six subjects in each group. One group ingested 9 g of the dahlia inulin juice per meal while the other ingested a placebo (maltodextrin, cellulose and coloring) containing 9 g of fiber per meal. The samples were mixed with water and ingested three times a day with meals for twenty-eight days. Fasting blood samples were drawn during preliminary screening, at the beginning of the study (day 0), at the end of week 3 (day 21) and the end of week 4 (day 28). The subjects continued their normal dietary routine and were not subjected to a low fat or low cholesterol diet. The range of cholesterol in the dahlia inulin juice group decreased by as much as 29 mg/dl and increased by as much as 20 mg/dl, with an average overall decrease between Day 0 and Day 28 of two points. The control group range of cholesterol decreased by only 8 points and increased as much as 32 mg/dl with an overall increase between Day 0 and Day 28 of 9 mg/dl. The dramatic decreases in cholesterol noted with those individuals who did not have intractable hypercholesterolemia was indicative that the dahlia inulin juice product appears to lower cholesterol in at least some forms of hypercholesterolemia.

EXAMPLE XV

Use of the Dahlia Inulin Juice Product in Increasing Physical Endurance—Healthy individuals between the ages of 20 and 50 who were not obese or had abnormal glucose tolerance tests were chosen for the study. A carbohydrate challenge was presented to them in a form of a meal which included one of the carbohydrates being investigated in the amount of 0.25 gram per kilogram body weight. After a twelve hour fast, and an initial blood glucose level check, the meal incorporating the carbohydrate was presented at 7:00 a.m. The meal consisted of approximately 600 calories, of which 40 percent was carbohydrates, 20 percent protein, and 40 percent fat. The meal consisted of oatmeal, whole milk, and the unknown carbohydrate. The carbohydrates that were evaluated during the study were glucose, fructose and the dahlia inulin juice product of this invention. Blood glucose were evaluated every 15 to 30 minutes at regular intervals over the next 10 hours following the meal. No other food material was ingested during that period. All samples were analyzed by the glucose oxidase method involving impregnated strips which were read by a scanner.

All subjects after consuming the meal with the dahlia inulin juice product were found to have a notable increase in blood glucose levels during the 3 to 6 hour period following the ingestion of the meal which was lacking or diminished in the fructose or glucose curves. This indicated a source or utilization of carbohydrate at a time beyond that of the fructose or glucose. It was also noted by the subjects that to perform the studies when inulin was used was easy with no ill effects, while on the days with fructose and glucose severe headaches and hunger caused difficulty in performing the study.

EXAMPLE XVI

Use of Specified Inulin Polymers in Promoting REM Sleep and Decreasing Insomnia—We noted during the testing of the above examples that inulin of these specified polymers in particular tended to increase the amount of REM sleep. Patients reported sleeping better and remembering their dreams very vividly during the time they were taking the inulin. A proposed method of insomnia usage would be to consume one teaspoon of powder as described in Example X before bedtime.

The usage of the dahlia inulin juice product of the present invention for insomnia is based in large part upon reports from users of the product or beverage powder of Mitchell, et al. U.S. Pat. No. 4,283,432, also referred to above. It is again noted that the beverage powder described in that invention has a relatively small portion, for example, between 20 and 30 percent, of its inulin polymers within the preferred range of the present invention.

Those reports indicate that, when an inulin polymer mixture is employed within dosage ranges as contemplated by the present invention, persons suffering particularly from insomnia are reported to sleep better and particularly to experience REM sleep as noted above.

It is hypothesized that the inulin juice polymer mixture of the present invention is effective in the control of insomnia because of the ability of inulin to be more available within the body, particularly to the brain.

As a further hypothesis, the treatment of insomnia by an inulin polymer mixture is further believed to be best achieved by use of the dahlia inulin juice product having greater than 50% of the inulin polymers in the range of DP 10–45, more preferably DP 16–40, in order to take advantage of the same factors noted, for example, in Examples XII–XVI.

The above reports concerning possible advantages of the present invention realized, for example, from use of the product or beverage powder of U.S. Pat. No. 4,283,432 also illustrate another novel feature of the present invention. Although the product or beverage powder of that patent was able to partially produce desirable effects as disclosed for the present invention, the remaining inulin polymers in the beverage powder in effect provided only a diluent factor which would have no substantial unique metabolic significance, again since it would be substantially (greater than 75%) formed of polymers less than DP 10 and therefore tending to be directly hydrolyzed to fructose and utilized as such within the body.

Accordingly, as noted above, the present invention particularly contemplates that the dahlia inulin juice product has at least about 50 percent and more preferably at least about 70 percent within preferred range of DP 10 to DP 45 in order to assure maximum or optimum effect for its use in supplying specific dietary needs or therapeutic applications as discussed above.

EXAMPLE XVII

Production of Inulin Juice Products from Other Plants

This example is intended to illustrate that other inulin bearing plants, particularly those of the Compositae family as listed above, can also be employed as a source for the inulin juice products of preferred polymer range and distribution as described above. Generally, these other plants are processed in the same manner described above with juice being pressed from the plants and initially assayed to determine the initial range and distribution of the inulin polymers. Processing conditions can then be selected and adjusted accordingly for realizing maximum or optimum formation of inulin polymers within the preferred range of DP 1–60 and having greater than 50% in the range of DP 10–45.

Referring again to Table 1, it may be seen that dahlia tubers are the most preferred source for the pressed juice containing the inulin polymer mixture of the present invention since dahlia tubers contain a substantially greater portion of inulin polymers within the preferred range of DP 10–45 and a significant distribution of polymers greater than DP 45. As disclosed above, the present invention permits the selection and adjustment of processing conditions so that the polymers above DP 45 can be converted into the preferred range of DP 10–45 in order to enhance metabolic value of the pressed juice containing the inulin polymer mixture of the present invention.

By contrast, the other inulin bearing plants, such as those listed in Table 1, contain substantially larger percentages of their inulin polymers within undesirable ranges below DP 10. These portions of the inulin polymer mixture obtained from such plants obviously do not contribute to the present invention, particularly because they tend to be hydrolyzed directly to fructose within the body as described above. We have also found that these larger percentages of inulin polymers below DP 10 inhibit drying of the polymer mixture to a solid. Accordingly, although an inulin polymer mixture of preferred polymer range and distribution can be formed from these plants in accordance with the present invention, production efficiency is substantially impaired since only a portion of the inulin polymers from those plants can be employed as discussed above.

EXAMPLE XVIII

Preparation and Use of Dahlia Inulin Juice Mixtures with a Portion Below DP 5

As noted above, the inulin juice mixture of the present invention is preferably maintained having greater than 50% of the inulin polymers within the range of DP 10–45. It was clearly indicated that polymers of a length greater than DP 45 are preferably hydrolyzed to within the preferred range of DP 10–45 in order to enhance permeability, selective utilization by Bifidus bacteria, and also to enhance unique metabolic value of the mixture for reasons discussed at length above. Polymers of less than DP 10 do not present a severe disadvantage, except in the case where the inulin juice mixture is being employed in the dietary use by diabetics. In such cases, polymers of less than DP 10 merely provide a source of fructose in the body which, if excessive, can be undesirable because of its effect on glycemia for the diabetic. However, even in this instance, a diabetic can assimilate a certain amount of inulin polymer less than DP 10 with the resulting fructose being formed in the body. However, it may be desirable that the inulin juice mixture of the invention employed for supplying specific dietary needs of the diabetics not have a portion below DP 10 in order to avoid exacerbating problems already present in the diabetic system.

For this reason, the inulin polymer mixture of the present invention is also preferably formed from dahlia tubers which, if freshly dug shortly following a killing frost, do not contain any substantial amount of inulin with polymers below DP 10.

However, even for this application, inulin from other plants can be employed. For example, in applications other than the dietary usage for diabetes, the inulin polymers of less than DP 10 can be available merely as a source of nourishment and may even be supplemented within the inulin juice polymer mixture, for example, to enhance flavor or taste of the resulting mixture.

It is also of course possible to remove cold water soluble inulin of less than DP 10, if necessary or desirable, for dietary usage in diabetes or promoting Bifidus selectively, by purification via ultrafiltration whereby these smaller molecules may be separated. Bifidus selectivity is promoted because the inulin polymers of less than DP 10 which can be utilized by pathogenic bacteria are being eliminated.

Accordingly, there has been discussed above numerous variations of processes for producing an inulin juice mixture having greater than 50% of the polymers in the range of DP 10–45, more preferably in the range of DP 16–40, together with a description of various methods of usage in supplying specific dietary needs based on unique metabolic and physical properties of the native, cold water soluble inulin juice mixture. Although numerous variations were described above, the preceding description is not to be taken as limiting the scope of the present invention which is defined only by the following appended claims.

Prior to the claims, a bibliography is set forth including listings for the various publications referred to in the preceding description. The references listed in the bibliography, as well as other references listed above within the description, are incorporated herein as though set forth in their entirety, at least to the extent necessary or desirable for assuring a more complete understanding and teaching of the present invention.

BIBLIOGRAPHY

1. Praznick, W. and Beck, R. H. F., *J. of Chromatography*, 348:187–197, (1985).
2. Jackson, R. F. and McDonald, E. J., *Bur. Standards J. Research*, 5:1151 (1930).
3. McDonald, E. J., *Advances in Carbohydrate Chemistry*, 2:253, Academic Press, Inc., N.Y. (1946).
4. Mitchell, W. A., Mitchell, C. E. and Mitchell, P. R., U.S. Pat. No. 4,285,735 (1981).
5. Phelps, C. F., *Biochem. J.*, 95:41–47 (1965).
6. Hill, R., U.S. Pat. No. 2,834,694 (1958).
7. Mitchell, J. C., *Br. J. of Dermatology*, 84:139–150 (1971).
8. Kosaric, N., Wieczorek, A., Cosentino, G. P., Duvnjak, S., Industrial Processing and Products from Jerusalem Artichoke, *Adv. Biochem. Eng./Biotechnol.*, 32 (Agric. Feedstock Waste Treat. Eng.), 1–24, (Eng), 1985.
9. Root, H. F. and Baker, M. L., *Arch. Intern. Med.*, 36:126–145 (1925).
10. Miller, B., Alving, A. S. and Rubin, J., *J. of Clinical Invest.*, 19:89–94 (1940).
11. Lewis, H. B., *J. Am. Med. Assoc.*, 58:1176 (1912).
12. Hue, L and Bartrons, R., *Regulation of Carbohydrate Metabolism*, Vol. I, Beitner, Rivka, CRC Press, Inc., Boca Raton, Fla. (1984).
13. Neely, P., El-Maghragi, M. R., Pilkis, S. J. and Claus, T. H., *Diabetes*, 30:1062–1064 (1981).

14. Davidson, M. B., *Diabetes Mellitus Diagnosis and Treatment*, 2nd Edition, page 49, John Wiley and Sons, Inc., N.Y. (1986).

What is claimed is:

1. A process for producing an inulin juice mixture suitable for usage in connection with conditions including (a) carbohydrate metabolic disorders, (b) diseases relating to carbohydrate metabolic disorders such as hypercholesterolemia, (c) weight control via dietary suppression, (d) providing physical stamina, and (e) selectively promoting Bifidus growth in the gut pressing juice from plants having substantial inulin content, assaying the pressed juice to determine its initial range distribution of inulin polymers and adjusting time and temperature of evaporation used in concentrating the pressed juice in order to convert the inulin polymers of the assayed juice to inulin polymers within the range of DP 1–55, having greater than 50% of the inulin polymers within the range of DP 10–45 and less than 10% of the polymers greater than DP 45 while maintaining the inulin in a stable polymorphic form having cold water solubility free from sesquiterpene lactones and also preserving the soluble non-carbohydrate components of the juice.

2. The process of claim 1 wherein the inulin containing plants are of the Compositae family.

3. The process of claim 2 wherein the inulin containing plants are dahlia tubers.

4. The process of claim 2 being carried out substantially without added chemicals or water in order to avoid the introduction of chemical impurities into the resulting juice containing the inulin polymer mixture.

5. The process of claim 4 wherein a substantial portion of the inulin juice polymer mixture has a final distribution of greater than 50% of the inulin polymer in the range of about DP 16 to DP 40.

6. The process of claim 4 wherein the assayed juice is concentrated, dried and pressed to an inulin juice polymer mixture having a form selected from the group consisting of syrups, powders and tablets.

7. The process of claim 6 wherein the inulin juice polymer mixture further has a form selected from the group consisting of syrups having about 25 to 80 percent soluble solids, powders of from about 50 to 200 mesh and tablets containing about 100 mg to 1000 mg of the inulin juice polymer mixture.

8. The process of claim 6 wherein the inulin juice polymer mixture is a powder suitable for being formed into tablets without the addition of a binder.

9. The process of claim 7 wherein sesquiterpene lactones from the resulting inulin polymer mixture have been substantially removed in order to avoid reactivity in sensitized individuals.

10. The process of claim 2 wherein the pressed juice is concentrated to a syrup having from about 25 to 80 percent soluble solids and at least about 90 percent of the inulin polymer mixture within the range of about DP 5 to DP 45.

11. The process of claim 10 wherein the pressed juice is concentrated to a syrup having at least about 70 percent soluble solids in order to maintain the cold water soluble polymorphic form of the inulin polymers.

12. The process of claim 10 wherein the syrup of from about 25 to 80 percent soluble solids is dried to a solid form having a moisture content no greater than about 10 percent.

13. The process of claim 2 wherein the extracted juice is assayed by high pressure ion chromatographic (HPIC) techniques.

14. The process of claim 13 wherein the pressed juice is concentrated to a syrup having at least about 70 percent soluble solids in order to maintain the cold water soluble polymorphic form of the inulin polymers.

15. The process of claim 13 wherein the syrup of from about 25 to 80 percent soluble solids is dried to a solid form having a moisture content no greater than about 10 percent.

16. The process of claim 1 wherein the assayed juice contains more than 10 percent inulin polymers of greater than DP 45, the process conditions thereupon comprising the steps of allowing the pressed juice to stand up to about 0 to 48 hours at room temperature and concentrating the pressed juice under reduced pressures at a temperature from about 50° C. to 100° C. or at atmospheric pressure at 100° C. to 129° C. for a period of time not greater than about 1 hour.

17. The process of claim 1 wherein the assayed juice contains less than 10 percent inulin polymers of greater than DP 45, the process conditions thereupon comprising the steps of allowing the pressed juice to stand up to about 6 hours at room temperature and concentrating the pressed juice under reduced pressures at a temperature from about 50° C. to 85° C. for a period of time not greater than about 1 hour.

18. The process of claim 1 wherein the assayed juice contains greater than 10 percent inulin polymers of less than DP 5, the pH of the pressed juice then being neutralized by alkali or ion exchanged to pH 7, the process conditions thereupon comprising the steps of allowing the pressed juice to stand up to about 48 hours at room temperature and concentrating the pressed juice under reduced pressures at a temperature from about 50° C. to 100° C. or at atmospheric pressures at 100° C. to 120° C. for a period of time not greater than about 1 hour.

19. The process of claim 1 further comprising the step of removing inulin polymers of less than DP 10.

20. The process of claim 1 wherein the inulin polymer mixture comprises a minor portion (less than 50 percent) having polydispersity of less than about DP 10 and being capable of being hydrolyzed to fructose in the body.

21. The process of claim 1 wherein at least about 50 percent of the inulin juice mixture contains polymers within the range of about DP 10 to 45.

22. The process of claim 21 wherein at least about 80 percent of the inulin polymers is within the range of about DP 10 to 45.

23. An inulin polymer mixture suitable for usage in connection with conditions of (a) carbohydrate metabolic disorders, (b) diseases relating to carbohydrate metabolic disorders as hypercholesterolemia, (c) weight control via dietary suppression, (d) providing physical stamina, and (e) selectively promoting Bifidus growth in the gut, the inulin polymers in the juice having >than 50% of its polymers in the range of about DP 10 to DP 45, the inulin polymer mixture being in a cold water soluble polymorphic form.

24. The inulin juice polymer mixture of claim 23 further characterized by substantial absence of sesquiterpene lactone to avoid dermatological or other types of undesirable reactivity in individuals.

25. The inulin juice polymer mixture of claim 24 being further characterized by a substantial portion of its polymers being in the range of about DP 16 to DP 40.

26. The inulin polymer mixture of claim 24 having a form selected from the group consisting of syrups, powders and tablets.

27. The inulin polymer mixture of claim 26 having a form selected from the group consisting of syrups having from about 25 to 80 percent soluble solids, powders of from about 50 to 200 mesh and tablets containing from about 100 mg to 1000 mg of the inulin polymer mixture.

28. The inulin juice polymer mixture of claim 26 in the form of a powder suitable for being compressed into tablets without the need for a binder component.

29. The inulin juice polymer mixture of claim 23 being a syrup having at least about 70 percent soluble solids in order to maintain its stable polymorphic form having cold water solubility.

30. The inulin juice polymer mixture of claim 23 being a solid and having a moisture content of no more than about 10 percent.

31. The inulin juice polymer mixture of claim 23 being formed by concentration of pressed juice from inulin bearing plants of the Compositae family.

32. The inulin juice polymer mixture of claim 31 being formed by concentration of pressed juice from dahlia tubers.

33. The inulin juice polymer mixture of claim 23 being at least about 50 percent within the polymer range of about DP 10 to 45.

34. The inulin polymer mixture of claim 33 being at least about 70 percent within the polydispersity range of about DP 16 to 45.

35. A method of treating an individual having at least one of the conditions of diabetes, or hypercholesterolemia, or of aiding an individual in the control of weight via dietary suppression, enhancement of physical stamina, and promotion of growth of Bifidus in the gut, comprising the steps of forming a juice containing an inulin polymer mixture having substantial cold water solubility wherein greater than 50% of its polymers are in the range of about DP 10 to 45, and administering the inulin juice polymer mixture to the individual in an amount of from 100 to about 10,000 mg.

36. The method of claim 35 wherein the form of inulin juice polymer mixture is selected from the group consisting of syrups, powders and tablets.

37. The method of claim 36 wherein the inulin juice polymer mixture has a form selected from the group consisting of syrups having from about 25 to 80 percent soluble solids, powders of from about 50 to 200 mesh and tablets having amounts of from about 100 mg to 1000 mg.

38. The method of claim 32 wherein the inulin juice polymer mixture is a powder suitable for being compressed into tablets without the need for a binder component.

39. The method of claim 35 wherein the inulin juice polymer mixture is formed by concentration of pressed juice from inulin bearing plants of the Compositae family.

40. The method of claim 35 wherein the inulin polymer mixture is formed by concentration of pressed juice from dahlia tubers.

41. The method of claim 35 wherein at least about 50 percent of the inulin polymer mixture is within the polymer range of about DP 10 to 45.

42. The method of claim 37 wherein at least about 70 percent of the inulin polymer mixture is within the polydispersity range of about DP 10 to 45.

43. The method of claim 35 wherein substantially all sesquiterpene lactone is removed from the inulin polymer mixture.

* * * * *